United States Patent [19]

Flesher et al.

[11] Patent Number: 5,213,766
[45] Date of Patent: May 25, 1993

[54] LIQUID COLLECTING APPARATUS FOR SAMPLE TESTING

[75] Inventors: Robert W. Flesher, Baltimore; Kevin J. Barnes, Uniontown, both of Md.

[73] Assignee: Apogee Designs, Ltd., Baltimore, Md.

[21] Appl. No.: 693,654

[22] Filed: Apr. 30, 1991

[51] Int. Cl.⁵ .............................................. G01N 1/10
[52] U.S. Cl. ..................................... 422/102; 422/101; 422/104; 422/58; 422/66; 436/44; 436/165; 436/170; 436/180; 436/809; 435/293; 435/294; 435/301; 435/809; 141/130; 73/864.53; 73/864.59; 73/864.72
[58] Field of Search ............... 422/100, 101, 102, 104, 422/56-58, 61, 69, 70, 66; 141/130; 436/44, 54, 162, 165, 169, 170, 180, 809; 435/293, 294, 300, 301, 310, 809, 810; 73/864.51, 864.53, 864.59, 864.72

[56] References Cited

U.S. PATENT DOCUMENTS

| | | | |
|---|---|---|---|
| 3,149,054 | 4/1962 | Ryan | 435/30 |
| 3,437,206 | 4/1969 | Kusik | 422/100 |
| 3,837,795 | 9/1974 | Becker et al. | 436/46 |
| 3,938,957 | 2/1976 | Lanier et al. | 422/104 |
| 3,961,346 | 6/1976 | White | 356/244 |
| 4,199,613 | 4/1980 | Johnson | 427/2 |
| 4,308,028 | 12/1981 | Elkins | 422/102 |
| 4,334,879 | 6/1982 | Fujimori | 422/100 |
| 4,377,641 | 3/1983 | Dee et al. | 436/178 |
| 4,444,062 | 4/1984 | Bennett et al. | 422/100 |
| 4,483,925 | 11/1984 | Noack | 436/809 |
| 4,498,510 | 2/1985 | Minshew, Jr. et al. | 422/100 |
| 4,501,496 | 2/1985 | Griffin | 356/246 |
| 4,511,534 | 4/1985 | Bennett, Jr. et al. | 422/100 |
| 4,518,565 | 5/1985 | Boger et al. | 422/58 |
| 4,626,509 | 12/1986 | Lyman | 435/293 |
| 4,731,335 | 3/1988 | Brigati | 436/180 |
| 4,798,706 | 1/1989 | Brigati | 422/102 |
| 4,940,853 | 7/1990 | Vandenburgh | 435/240.23 |

Primary Examiner—Lynn M. Kummert
Attorney, Agent, or Firm—Jacobson, Price, Holman & Stern

[57] ABSTRACT

For collecting a batch of liquid samples, such as in the laboratory testing of body fluids, there is provided a collecting sheet having an array of resiliently deflectable fingers formed in the sheet. The fingers can be deflected out of the plane of the sheet to dip into respective liquid containers such as wells in a microtiter plate so as to absorb liquid samples therefrom. When released, the fingers snap back into the plane of the sheet retaining the liquid samples therein.

23 Claims, 4 Drawing Sheets

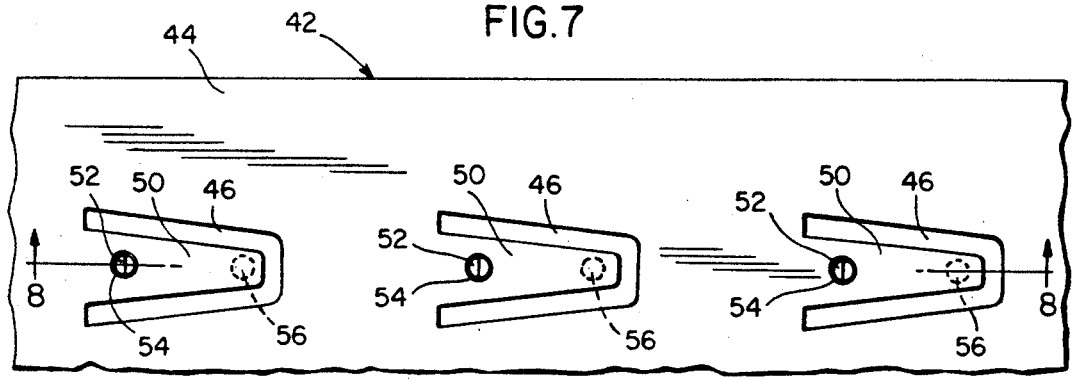
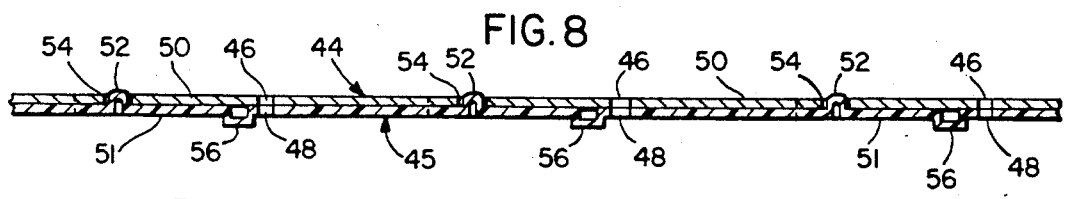
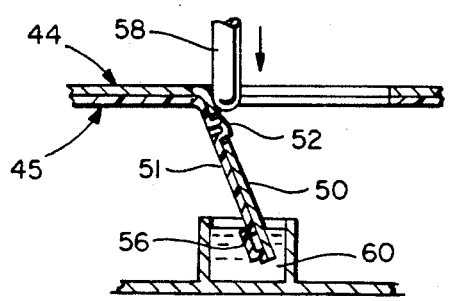
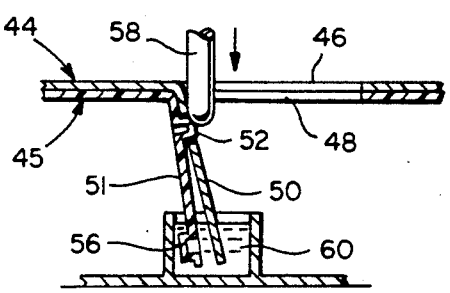
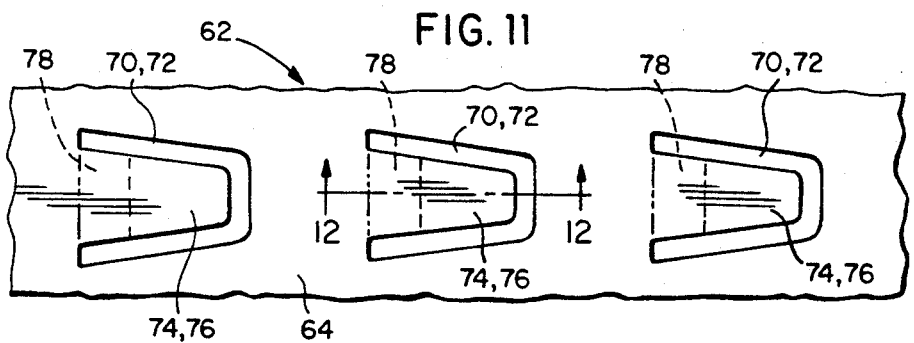
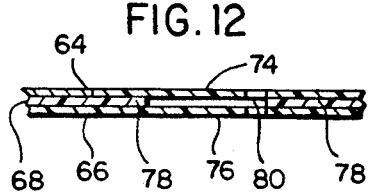
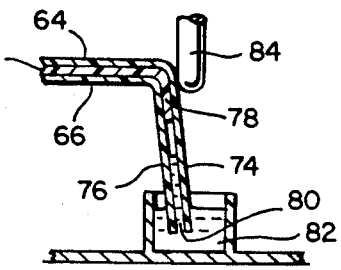

LIQUID COLLECTING APPARATUS FOR SAMPLE TESTING

BACKGROUND OF THE INVENTION

This invention relates to liquid collecting apparatus particularly useful in sample testing where it is necessary to handle small metered quantities of liquids in batches.

For example, in the laboratory testing of body fluids such as blood or urine, it is commonly necessary to mix metered amounts of the fluid with different chemicals or reagents in order to perform particular tests on the fluid. Accordingly, there is a need in such testing for a device which can handle, as a batch, small metered quantities of the fluid or a test liquid. The device may be used, for example, to deliver the metered quantities of fluid to a test plate such as a microtiter plate having a batch of wells each containing a different chemical or reagent, so that the separate fluid samples in the device can be mixed with the different liquids in the plate. Alternatively the device may be used to receive samples of liquid from a reservoir or a microtiter plate and hold for transfer the samples to a subsequent test station for mixing with the body fluid.

One known form of device for use in the batch-wise handling of metered liquid test samples comprises, for example, a base member or the like from which are suspended an array of sampling tubes, or pipettes which when dipped into a liquid, will each adsorb an equal amount of the liquid by capillary action. A device of this nature tends to be somewhat cumbersome, particularly where it is required for storage of the liquid samples such as for subsequent testing.

Other known forms of liquid handling device for laboratory testing utilize batch-wise arrays of absorbent cards and the like associated with different forms of holder for receiving the metered sample batches.

SUMMARY OF THE INVENTION

It is an object of the invention to provide a novel form of liquid collecting device for the batch-wise handling of liquid samples which device is simple to manufacture and use, which is inexpensive to produce in bulk and which is extremely compact to transport and store.

A further object of the invention is to provide a liquid collecting device for batch-wise handling of liquid samples which device is embodied in a substantially planar sheet or card having discrete portions which can be resiliently deflected out of the plane of the sheet or card to pick up metered samples of liquid and then released back into the plane of the sheet or card for storage or transport of the liquid samples.

Another object of the invention is to provide a sheet or card of resilient material having an array of discrete portions, conveniently arranged in rows and columns, and which can be resiliently deflected out of the plane of the sheet or card for insertion into an equivalent array of liquid receptacles for absorbing a quantity of liquid from the respective receptacle, and which when released can revert substantially to its initial state within the plane of the sheet or card for transport or storage of the liquid.

Broadly stated therefore, in pursuit of the above and other objects, the invention provides a device for batch-wise collecting of small metered quantities of liquid comprising a substantially planar sheet or card having an array of openings such as cutouts defining a plurality of discrete fingers, conveniently arranged on the sheet or card in rows and columns, each finger being resiliently deflectable out of the plane of the sheet or card for dipping at least a tip portion of the finger into a liquid container to absorb a quantity of liquid in the tip portion and the finger, when released, being adapted to return substantially into the plane of the sheet or card for transport and/or storage of the liquid.

In use, in accordance with another aspect of the invention a sheet or card as described above may be located over a microtiter or like plate having an array of liquid receptacles, the number and configuration of card fingers being related to the number of receptacles in the plate. Apparatus including a batch of equally related vertical pins ma then be used to depress the fingers simultaneously into the microtiter containers by lowering the pins into contact with the respective fingers. Then, after absorption a liquid from the receptacles by the fingers, the pins are lifted to release the fingers back into the plane of the sheet or card.

In an alternative method of use, a strip of material formed with the deflectable fingers may be rolled around a rod or like guide member having an axis extending transversely to the length of each finger whereby the finger or a row of fingers is deflected as the sheet moves around the rod. A liquid container or containers can be moved adjacent the rod in timed relation to the movement of the strip, so that while deflected, each finger will dip into a liquid container. Then, as the fingers move off and away from the rod they return into the plane of the strip.

Different preferred forms of card and finger structures according to the invention will be described in detail hereafter.

It will be apparent that the invention provides an exceedingly simple and economical form of liquid handling device particularly suited to the batch-wise transfer and storage of small quantities of liquid such as used in laboratory sample testing. Moreover, the device, with or without the liquid samples in place, can be shipped and stored in a flat compact state having a minimum space requirement.

Additional features and advantages of the invention will be apparent from the ensuing description and claims read in conjunction with the attached drawings.

BRIEF DESCRIPTION OF DRAWINGS

FIG. 7 is a view similar to FIG. 1 of a card having a further form of deflectable finger structure, FIG. 8 is a sectional view on line 8—8 of FIG. 7, FIGS. 9 and 10 are sectional elevational views showing how the finger structure shown in FIGS. 7 and 8 is deflected to receive liquid from a container, FIG. 11 is a plan view of a part of a card having a still further form of deflectable finger structure, FIG. 12 is a sectional view on line 12—12 of FIG. 11, FIG. 13 is a sectional elevational view showing how the finger structure shown in FIGS. 11 and 12 is deflected to receive liquid from a container.

DESCRIPTION OF PREFERRED EMBODIMENTS

Figure 1:
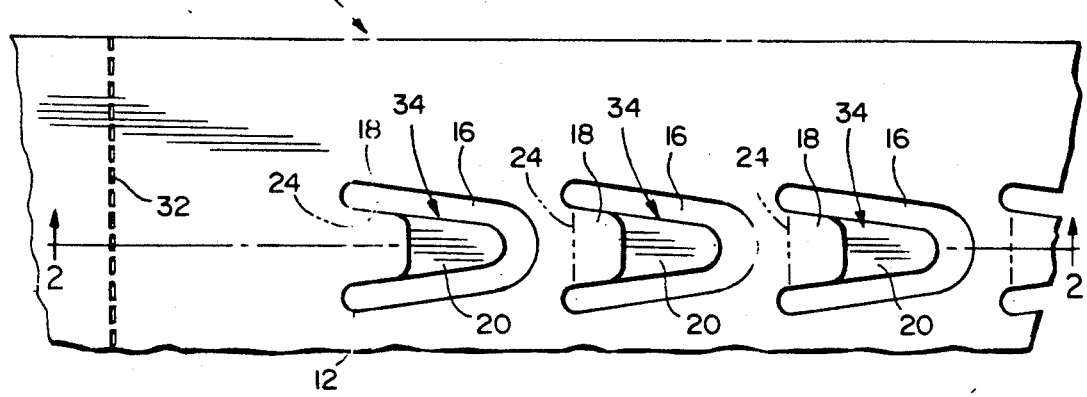
FIG. 1 is a plan view of a part of one form of liquid collecting card in accordance with the invention.
Figure 2:
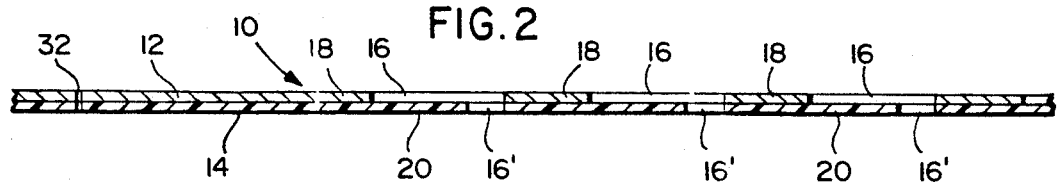
FIG. 2 is a sectional view on line 2—2 of FIG. 1.

Referring initially to FIGS. 1 and 2, there is illustrated a portion of a laminated liquid collecting card 10 having an upper layer 12 and a lower layer 14. The upper layer is made of a resilient material such as, for example, a polycarbonate material of about 0.007 to 0.010 inch in thickness which can be printed upon, which can be resiliently bent through 90° and which, when released will return substantially to its original plane. Further, the upper layer 12 is formed with rows and columns of substantially horseshoe-like cutouts 16 each of which defines at one end thereof a shortish stubby finger-like protrusion 18.

The lower layer 14 of the card is made of an absorbent Nylon material (known per se) which has a microporous-like structure capable of absorbing liquid. The Nylon is laminated to the upper layer by suitable adhesion or welding and is provided with rows and columns of cut-outs 16' which are aligned and register with the cut-outs 16 in the upper layer. The cut-outs 16' in the lower layer however define at the respective left hand ends longer finger-like protrusions 20 which extend beyond the ends of protrusions 18.

Figure 4:
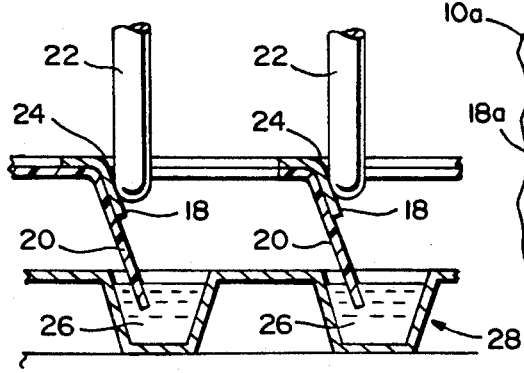
FIG. 4 is a sectional elevational view showing how finger portions of the card can be deflected into respective liquid containers.

As shown in FIG. 4, the finger-like protrusions 20 can be deflected downwardly out of the plane of card 10 by vertically movable pins 22 disposed so as to push down on the upper layer protrusions 18 deflecting same about bend lines 24 which may be impressed in the card. Thus the protrusions 20 can be caused to dip at their ends into liquid contained in reservoirs 26 which may, for example, comprise respective containers of a microtiter plate 28. When dipped into the liquid, the protrusions 20 will each absorb a quantity of liquid due to the porous nature of the Nylon material. When the pins 22 are raised, the protrusions 18 and 22 spring resiliently back into the plane of card 10.

Figure 3:
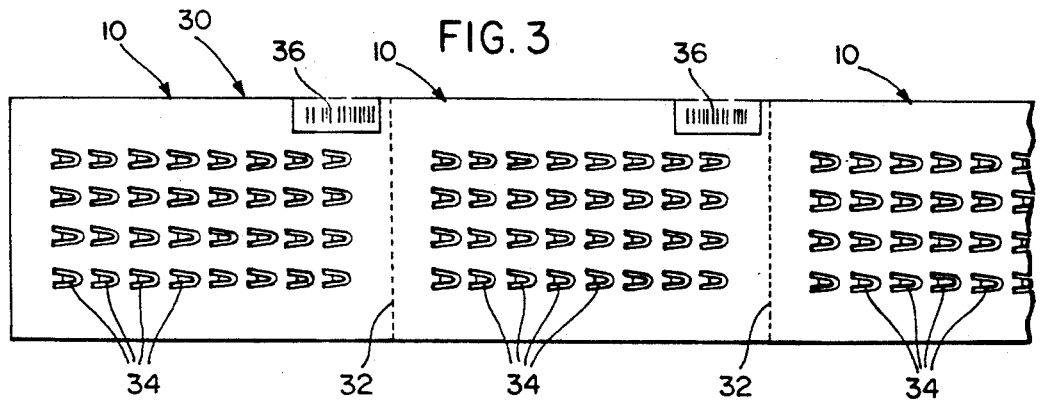
FIG. 3 is a reduced scale plan view of a sheet comprising a line of attached cards according to FIGS. 1 and 2.

FIG. 3 shows a sheet 30 which is divided by perforations 32 into a line of cards 10 each having a like number of depressible finger elements 34 (a finger element 34 being defined as the combination of the protrusions 18 and 20 described above) arranged in respective rows and columns. Each card may, as shown, be printed with a bar code 36 or other identification means.

Figure 5:
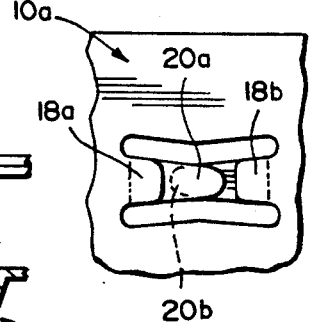
FIG. 5 is a plan view of a part of a different form of liquid handling card having deflectable twin finger structures.
Figure 6:
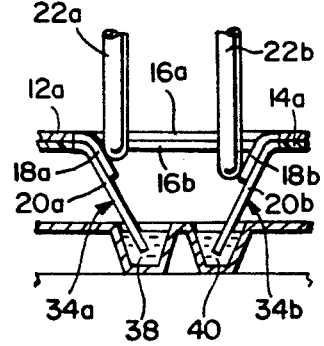
FIG. 6 is a view similar to FIG. 4 showing deflection of a twin-finger structure.
Figure 14:
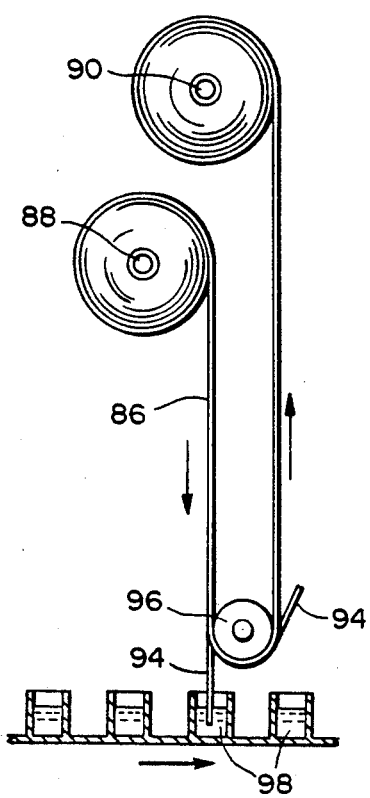
FIGS. 14–16 are somewhat diagrammatic sequential views showing liquid handling strips in reel-form having deflectable fingers according to the invention and how the fingers are deflected into liquid containers.
Figure 15:
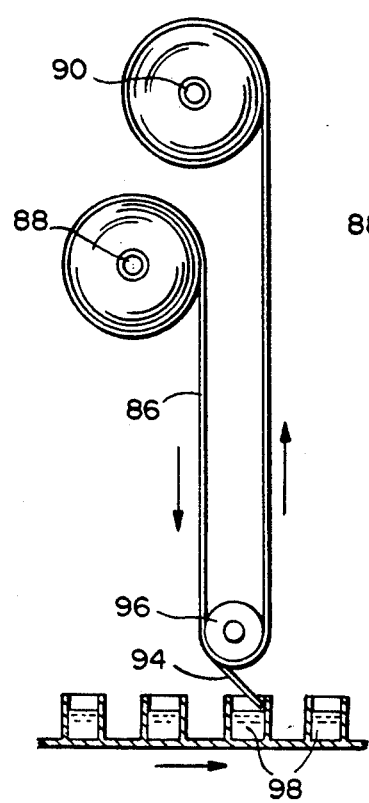
Figure 16:
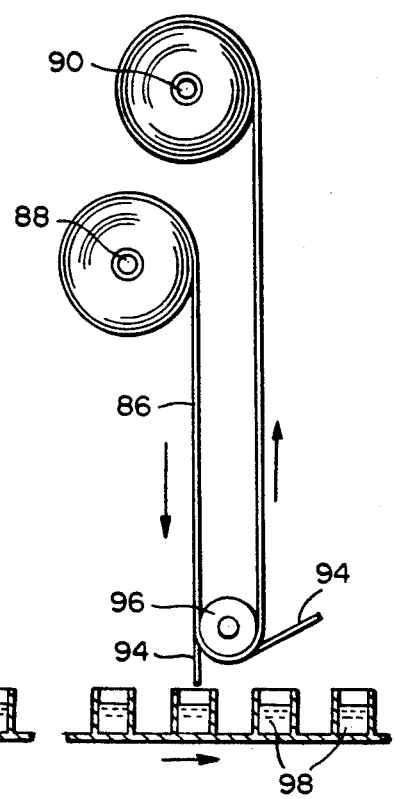
Figure 17:
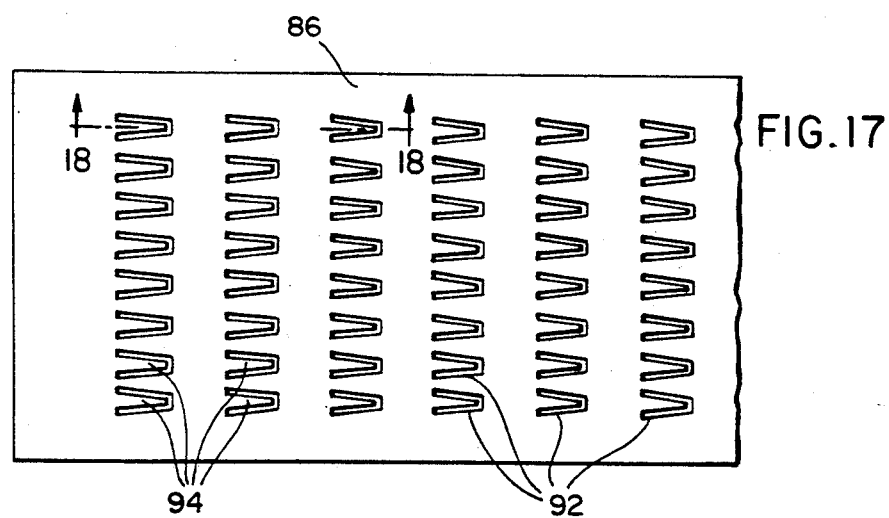
FIG. 17 is a plan view of part of a sheet according to the invention suitable for use in accordance with FIGS. 14–16.
Figure 18:
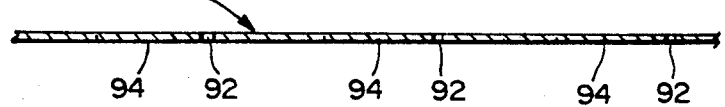
FIG. 18 is a sectional view on line 18—18 of FIG. 17.

FIGS. 5 and 6 show a modified laminated card where the depressible finger elements 34a and 34b are arranged in opposed overlapping pairs, the cut-outs 16a and 16b in the upper and lower layers 12a and 14a of the card being correspondingly shaped. The card construction is otherwise like that described in relation to FIGS. 1–3. The opposed finger arrangement is useful, for example, where it is necessary to mix absorbed quantities of different liquids 38, 40 when the respective protrusions 20a and 20b are brought back together in the plane of card 10a. As shown in FIG. 6, the fingers 34a and 34b are depressed by pins 22a and 22b which are somewhat offset vertically so that one finger is depressed before and returns after the other finger thereby preventing interference of the fingers. While FIGS. 5 and 6 show only two overlapping fingers, it also is possible to provide a structure including three or more such overlapping fingers.

In FIGS. 7 to 10, there is shown another type of card 42 laminated from upper and lower layers 44, 45 of resilient material, such as card stock or plastic, each layer being formed with columns and rows of horseshoe-shaped cut-outs 46, 48 defining upper and lower finger elements 50, 51 of like dimensions which are themselves free from lamination. Each of the lower finger elements is formed with an upwardly extending indent 52, which fits in a corresponding aperture 54 formed in the upper finger 50, and further the lower finger, near its tip is formed with a downwardly indented well 56. In use, the respective finger structures are deflected downwardly out of the plane of card 42 by respective pins 58 positioned to press on the respective fingers near the base end of each finger in order to cause the tip ends of the fingers to dip into respective liquid reservoirs 60. Then, when the pin engages the protruding indent 52, further downward movement of the pin (FIG. 10) causes separation of the fingers 50 and 51, and opening of the well 56 to receive liquid. When the pin 58 is raised, indent 52 is released causing fingers 50 and 51 to close thereby trapping the liquid in well 56. Further raising of the pin allows the finger structure to snap back into the plane of the card as previously.

FIGS. 11 to 13 show a three-layer laminated card structure 62 comprising an upper layer 64, a lower layer 66 and a central layer 68. The upper and lower layers have substantially identical horseshoe-shaped cut-outs 70, 72 defining elongate upper and lower fingers 74, 76, but the central layer has cut-outs defining shorter fingers 78. Accordingly a narrow space 80 is left between the tip ends of the upper and lower fingers, which forms a pipette-like structure which attracts liquid by capillary action when the finger assembly is resiliently deflected into a liquid reservoir 82, by pin 84. As in the previous embodiments, when the pin releases the finger structure, it snaps back into the plane of the card trapping the liquid between the upper and lower fingers.

In FIGS. 14–18 there is shown a liquid pick-up sheet in the form of a long single-layer strip 86 of resilient absorbent material wound on respective feed and receiving rolls 88 and 90. The strip is again formed with rows and columns of horseshoe-shaped cut-outs 92 defining resilient fingers 94. The strip is fed continuously in the direction of the arrows in FIGS. 14–16 down and up around a guide rod 96 or the like. As the respective rows of fingers 94 transverse the rod 96, they are deflected as shown, out of the plane of strip 8 and into respective liquid containers 98 which may be moved as shown, in a horizontal direction perpendicularly to the movement of the strip. If appropriate, a large stationary liquid reservoir may also be used. As the fingers move upwardly, out of the liquid, and away from rod 96, they snap back as in the previous embodiments, into the plane of the strip.

Figure 19:
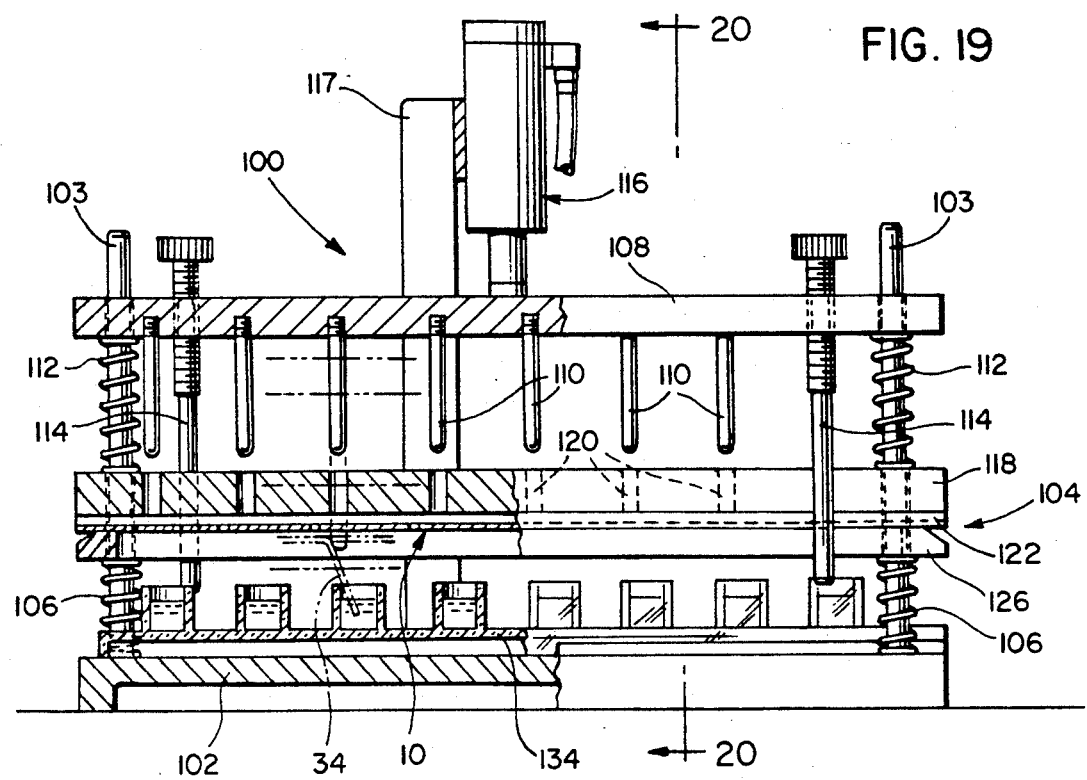
FIG. 19 is a side elevational view of an apparatus for use in the batch-wise deflecting of the fingers of a card according to the invention into corresponding liquid containers.
Figure 20:
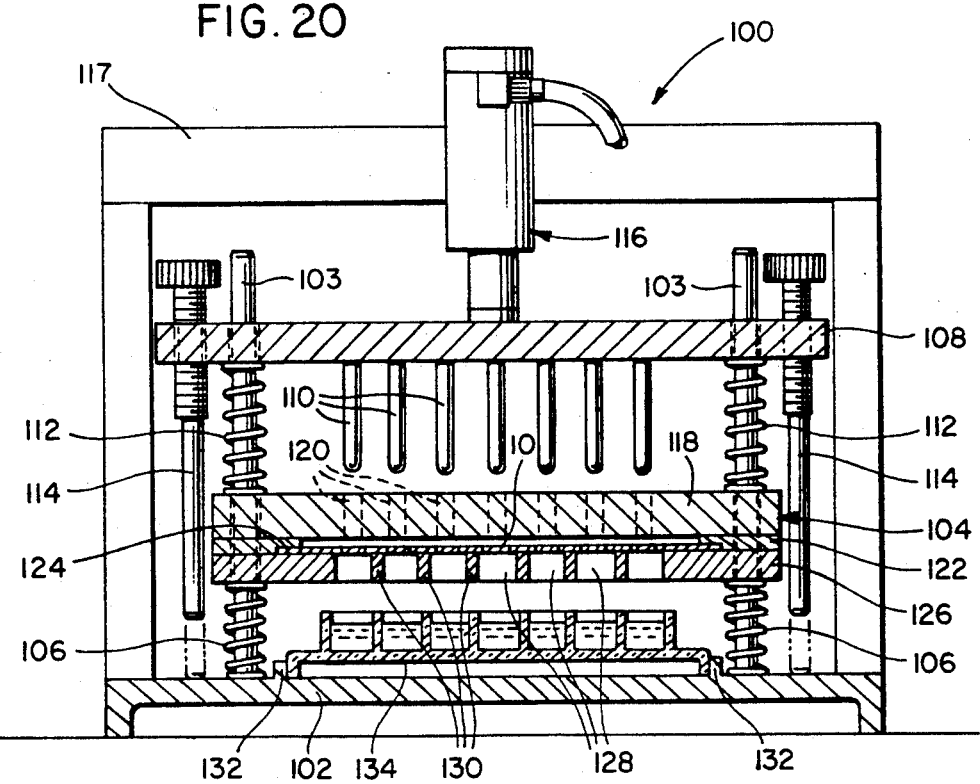
FIG. 20 is a sectional view on line 20—20 of FIG. 19.

FIGS. 19 and 20 show an apparatus 100 which can be used for deflecting the resilient finger elements of cards as shown in the previously described embodiments of FIGS. 1-13. Apparatus 100 comprises a base 102 supporting four upright posts 103. On the posts is mounted a reciprocable card holder 104 resting on first compression springs 106 which surround the posts between the holder and the base. A platen 108 with depending pins 110 is mounted on the posts above holder 104 with interposed second compression springs 112 also surrounding the posts. The spring force of springs 106 is greater than that of springs 112. The platen 108 carries screw-adjustable vertical stop pins 114 for limiting movement of the platen towards the base. A pressure fluid piston-cylinder assembly 116 is mounted on a frame 117 on the base for applying downward pressure on the platen.

The card-holder 104 includes a top plate 118 with bores 120 for passage of the pins 110, a central plate 122 with slides 124 for receiving opposite edges of a card, such as card 10 (FIGS. 1-3) and a lower plate 126 with channels 128 and lands 130. The lands 130 are positioned to support card areas between the finger elements while the channels provide accommodation for the deflecting finger elements.

The base 102 is provided with guides 132 for a liquid container, such as a microtiter plate 134. It will be understood that the apparatus is designed to provide mutual alignment of the pins 110, the finger elements 34 in card 10, and the liquid containers in the microtiter plate.

When downward pressure is applied to the platen 108 by the piston cylinder assembly 116, the platen moves downwardly in preference to the card holder 104 due to the lighter force in springs 112, so that the pins 110 pass through the bores 120 in plate 118, engage the finger elements 34 of the card and deflect the elements downwardly through the channels 128. Then, with increasing compression of the springs 112, holder 104 is also forced down overcoming the pressure of springs 106 and causing the tips of the fingers 34 to dip into the liquid containers in the microtiter plate. The two-stage downward movement of the apparatus is preferred so that the fingers will be in a somewhat vertically extending orientation when dipped into and removed from the liquid.

When the piston cylinder assembly is retracted, first the holder 104 and platen 108 will move up as a unit under the influence of the stronger springs 106, withdrawing the fingers from the liquid containers. Then, the platen will move up relative to holder 104 thereby withdrawing the pins 110 from the fingers and allowing the fingers to snap back into the plane of the card.

It is possible to incorporate test or other solution, wet or dry, in or on any of the above-described finger structures to be activated by, or mixed with liquid collected during the finger dipping process. In FIGS. 1-6 and 14-18, the solution can be pre-absorbed in the fingers. In FIGS. 7-10 the solution can be contained in cups 56. In FIGS. 11-14 the solution can be contained in space 80.

While only preferred embodiments of the invention have been described in detail, the invention is not limited thereby and modifications can be made within the scope of the attached claims.

We claim:

1. A device for batch-wise collecting of discrete quantities of liquid comprising a substantially planar sheet having an array of openings therein defining a plurality of discrete finger elements, each finger element constructed and arranged to be resiliently deflectable out of the plane of the sheet for dipping at least a tip portion of the finger element into a liquid container for collecting a quantity of liquid in at least the tip portion, and said finger elements when released being constructed and arranged to return substantially into the plane of the sheet for retention of the liquid.

2. A device as claimed in claim 1 wherein said openings comprise substantially horseshoe-shaped cut-outs, each defining an elongated tapering finger element.

3. A device as claimed in claim 1 wherein the finger elements are arranged on the sheet in spaced rows and columns perpendicular to the rows.

4. A device as claimed in claim 1 wherein a plurality of sheets are provided and connected end-to-end to form an elongate strip of sheets 5. A device as claimed in claim 4 wherein respective sheets in the strip are connected to adjacent ones thereof by transverse tear lines.

6. A device as claimed in claim 4 wherein the strip is wound on respective feed and take-up rolls and passes around a guide arranged between the rolls to provide means for deflection of the finger elements out of the plane of the strip with passage around the guide.

7. A device as claimed in claim 6 in combination with liquid container means positioned for receiving each of the tip portions of the respective finger elements as they are deflected out of the plane of the strip with passage around the guide.

8. A device as claimed in claim 1 wherein the finger elements are arranged in opposed overlapping pairs.

9. A device as claimed in claim 1 wherein at least the tip portion of each finger element is formed of absorbent material.

10. A device as claimed in claim 9 wherein the sheet is formed of absorbent material.

11. A device as claimed in claim 10 wherein the sheet is a single layer sheet.

12. A device as claimed in claim 1 wherein the sheet comprises laminated upper and lower layers, the upper and lower layers being formed with respective finger formations defining the respective elements, the finger formations of the lower layer having tip ends extending beyond the respective finger formations of the upper layer and being provided with absorbent material.

13. A device as claimed in claim 1 wherein the sheet comprises laminated upper, lower and central layers, each finger element including a finger tip portion on the upper layer, a corresponding finger tip portion on the lower layer and a space between the tip portions defined by a finger-stub portion of the central layer, said space being dimensioned to receive liquid by capillary attraction when the finger element is dipped in liquid.

14. A device as claimed in claim 1 wherein the sheet comprises laminated upper and lower layers, the finger elements each comprising non-laminated portions of the respective layers constructed and arranged to separate when the respective finger element is deflected out of the plane of the sheet to receive liquid therebetween.

15. A device as claimed in claim 14 wherein each non-laminated portion of the lower layer is formed with a well to receive liquid when the non-laminated portions separate, the well being covered by the non-laminated portion of the upper layer when the respective finger element is in the plane of the sheet.

16. A device as claimed in claim 15 wherein each non-laminated portion of the lower layer is formed with a protrusion for receipt in a corresponding opening formed in the respective non-laminated portion of the upper layer, said protrusion when engaged by a pusher which provides deflection of the finger element, being constructed for providing separation of the non-laminated portions.

17. A method of collecting batch-wise samples of liquid comprising providing a substantially planar collecting sheet having therein an array of resiliently deflectable finger elements with a tip portions constructed and arranged to collect liquid, positioning the sheet over liquid container means, resiliently deflecting the finger elements out of the plane of the sheet causing the respective tip portions to dip into liquid in the container means thereby each collecting a quantity of liquid, and causing the finger elements to return substantially into the plane of the sheet retaining the collected liquid.

18. A method a defined in claim 17 wherein the finger elements are deflected out of the plane of the sheet by engaging respective ones of the elements with respective pusher means and the elements are caused to return into the plane of the sheet by disengagement of the pusher means.

19. A method as defined in claim 17 wherein the finger elements are deflected out of the plane of the sheet by continuously moving the sheet around a guide and the elements are caused to return into the plane of the sheet by movement off the guide.

20. A method as claimed in claim 17 including the step of incorporating a solution in or on said finger elements prior to said deflecting step for being mixed with or activated by said liquid.

21. Apparatus for collecting a batch of liquid samples comprising a sheet having an array of resiliently deflectable liquid collection fingers, a base receiving liquid container means, a holder for supporting said sheet, mounting means for mounting the holder above the liquid container means, a platen with an array of depending pins corresponding to the fingers in the sheet, further mounting means for mounting the platen for vertical reciprocation above the holder, and means for providing vertical reciprocation of the platen causing the pins on a downstroke of the platen to engage respective fingers of a sheet in the holder and deflect the fingers downwardly for dipping into liquid in the container means, further causing the pins on an upstroke of the platen to release the fingers back into the plane of the sheet.

22. Apparatus as defined in claim 21 wherein the holder and the platen are each vertically reciprocally mounted on vertical posts extending from the base, the mounting means for the holder including first coil compression springs around the respective posts between the base and the holder, the further mounting means for the platen including second coil compression springs around the respective posts between the holder and the platen, the second springs having a lighter spring force than the first springs.

23. Apparatus as defined in claim 22 wherein the holder comprises a top plate with bores for passage of the pins, a center plate with a slide for receiving said sheet, and a bottom plate with lands for supporting parts of the sheet between the fingers and channels between the lands for accommodating the fingers as they are deflected.

* * * * *